(12) United States Patent
Schaefer et al.

(10) Patent No.: US 8,642,326 B1
(45) Date of Patent: Feb. 4, 2014

(54) SYSTEM FOR THE PRODUCTION AND HARVESTING OF ALGAE

(76) Inventors: Alan W. Schaefer, Ste. Genevieve, MO (US); Brandon D. Cabot, Ste. Genevieve, MO (US)

( * ) Notice: Subject to any disclaimer, the term of this patent is extended or adjusted under 35 U.S.C. 154(b) by 559 days.

(21) Appl. No.: 12/874,751

(22) Filed: Sep. 2, 2010

Related U.S. Application Data (60) Provisional application No. 61/239,306, filed on Sep. 2, 2009.

(51) Int. Cl.
*C12M 1/00* (2006.01)
*C12M 3/00* (2006.01)
*C12N 1/12* (2006.01)
*A01G 7/00* (2006.01)
*A01H 13/00* (2006.01)

(52) U.S. Cl.
USPC ..... 435/292.1; 47/1.4; 435/257.1; 435/283.1; 435/289.1

(58) Field of Classification Search
USPC ............ 435/257.1, 283.1–309.4; 47/1.4
See application file for complete search history.

(56) References Cited

U.S. PATENT DOCUMENTS

| | | | | |
|---|---|---|---|---|
| 3,959,923 A | * | 6/1976 | Selke | 47/1.4 |
| 4,267,038 A | * | 5/1981 | Thompson | 210/602 |
| 2006/0257295 A1 | * | 11/2006 | Chen et al. | 422/139 |
| 2010/0190227 A1 | * | 7/2010 | Dauth et al. | 435/168 |

\* cited by examiner

*Primary Examiner* — Nathan Bowers
*Assistant Examiner* — Lydia Edwards
(74) *Attorney, Agent, or Firm* — Grace J. Fishel (57) ABSTRACT

A system for the production and harvesting of algae including one or more of the following components: A turbulator for dissolving carbon dioxide in water to form an algae growth media, a photobioreactor having a serpentine flow path for the algae growth media through spaced apart high and low baffles with an associated light source, a dewatering device for the algae slurry harvested from the photobioreactor, a turbulator for breaking up the cells in the algae sludge coming off the dewatering device, a cooker for cooking the broken up algae cells under pressure and a settling tank for separating the cooked cells into oil, spent media and biomass fractions.

16 Claims, 12 Drawing Sheets

SYSTEM FOR THE PRODUCTION AND HARVESTING OF ALGAE

This application claims priority from provisional application Ser. No. 61/239,306, filed Sep. 2, 2009, for Photobioreactor for Production of Algae and Methods.

BACKGROUND OF THE INVENTION

1. Field of the Invention

The present invention relates to a comprehensive system for the production and harvesting of algae including as one component a photobioreactor for optimizing algae growth for use in carbon dioxide sequestration and biomass and biofuel production.

2. Brief Description of the Prior Art

Algae perform biosynthesis of carbon dioxide. In the past, algae have been commercially cultivated in ponds, raceways, tubes, liquid membranes and panels.

In pond cultivation, concrete-made open cultivation ponds are built outdoors filled with water and algae are cultured using available sunlight. A high concentration of algae cells form a thick blanket of algae on top, which inhibits sunlight penetration. Unless the algae cell density is reduced in the top few centimeters, the total algae photosynthetic efficiency is lowered. Hence it is necessary to stir the water in the pond and to keep the depth of pond to about 15 cm or less. Stirring requires a large amount of energy and the required land for the shallow ponds is vast. Further, since the cell density in the ponds must be kept low, the biomass must be harvested from a huge amount of low density culture solution. In addition, because the cultivation pond is open and located outdoors, dust, waste and airborne microorganisms may contaminate the pond making it impossible to maintain an algae culture of high purity and quality. The cultivation pond is also subject to temperature fluctuations and, in certain locations, freezing.

Open ponds can be replaced with raceway type vessels which consist of a long, narrow open cultivation tank with a divider down the middle to form a circular path. The algae are then mechanically circulated around the raceway in a continuous circle. This system creates an improved circulation system, but the photosynthetic rate of algae is low, similar to that in a cultivation pond. Light is not efficiently used, carbon dioxide conversion is low and the mechanical stirring of the algae results in broken cells due to shear stress. This causes a reduction of cellular activity resulting in a low propagation rate. The negative aspects of limited sunlight, temperature fluctuations and culture contamination still apply in the open raceway system.

In tubular type cultivation, algae are cultivated in a light transmission tube. Algae cultivation using this apparatus protects the culture from contamination by foreign microorganisms, leading to a high culture concentration. In due course of operation, however, algae attach to the internal wall of the tube reducing light being passed through the tube which reduces algae cultivation. Removal of the algae attached to the internal wall of the tube is difficult. Growth of the algae is further inhibited by the presence of oxygen which is a byproduct of photosynthesis and collects in the tube.

In a liquid membrane-forming cultivation apparatus, a dome-shaped, light-passing lid body is installed on a top face of a small cultivation vessel. A culture solution is jetted from a bottom to an internal face of an apical part of the dome-shaped lid body to form a liquid membrane on the internal face of the lid body where it is irradiated with light. This system requires a circulation pump for continual formation of the liquid membrane and is not suitable for mass cultivation.

A panel type cultivation apparatus makes use of a thin box-like apparatus, which is prepared by using two resin-made panel boards, with inclination. The panel type also relies on sunlight for algae photosynthesis. The panel is a closed system similar to the tubular type cultivation apparatus and, accordingly, has an advantage of no contamination of the culture solution by stray microorganisms, dirt and waste. However, the buildup of oxygen once again stays in the apparatus and inhibits algae growth. When solar energy is used for photosynthesis another problem arises. As the altitude of the sun changes throughout the day and through the seasons, the sunlight incident angle to a surface of the apparatus changes resulting in an insufficient total amount of sunlight received per unit area.

Algae accumulate useful substances in their bodies by photosynthesis. Photosynthesis may be promoted by increasing the light-receiving area of the cultivation apparatus, efficiently stirring the culture solution, adjusting the thickness or a depth of the culture solution, removing and cleaning the algae cells attached to the internal surface of the cultivation apparatus, regulating the temperature, preventing contamination with dust, waste, bacteria, and other algae species and so forth. None of these prior art systems optimize algae growth. For example, with ponds the light-receiving area can be increased only by increasing the area of the pond. Stirring breaks up the cells. Temperature can be regulated by pumping cold water into the prior art apparatus. This however results in a diluted solution being harvested with low algae density.

Hence the conventional methods described above each have pros and cons and none provide solutions to all the issues involved in large scale emissions (e.g., +25,000 cfm) of greenhouse gases.

BRIEF SUMMARY OF THE INVENTION

In accordance with the invention, a comprehensive system is provided for the production and harvesting of algae, said system comprising several components which either work separately or in concert. One component is a photobioreactor having a serpentine flow path for an algae growth media through spaced apart high and low baffles. The photobioreactor has a cover and a light source associated with the baffles. An algae slurry is formed as the algae growth media flows through the photobioreactor. Another part of the system is a turbulator with fixed and rotating discs which create sufficient turbulence to dissolve carbon dioxide in water to which nutrients have been added to form an algae growth media as the water flows through the turbulator. A dewatering device may be provided for dewatering the algae slurry as it exits the photobioreactor, one such device being a vibrating screen. A second turbulator may be used to break up the cells in the algae sludge coming off the dewatering device or devices. The second turbulator, like the first turbulator described above, has fixed and rotating discs which create sufficient turbulence to break up the algae sludge as it flows through the turbulator. The appropriate size of the discs, number of discs, spacing, rotation speed, transit time, etc. that is functionally necessary for each of the turbulators can be determined empirically. Algae cells from the second turbulator may be further processed in a pressure cooker and the cooked algae then separated into oil, spent media and biomass fractions. The system may be operated either in a batch mode or continuously with spent media reconditioned and recycled to the photobioreactor along with undissolved carbon dioxide collected under the cover of the photobioreactor. Oxygen which is a byproduct of algae photosynthesis may be collected for use, as may the remaining biomass.

The invention summarized above comprises the constructions hereinafter described, the scope of the invention being indicated by the subjoined claims.

BRIEF DESCRIPTION OF THE SEVERAL VIEWS OF THE DRAWING

In the accompanying drawings, in which several of various possible embodiments of the invention are illustrated, corresponding reference characters refer to corresponding parts throughout the several views of the drawings in which.

DETAILED DESCRIPTION OF THE INVENTION

Figure 1:
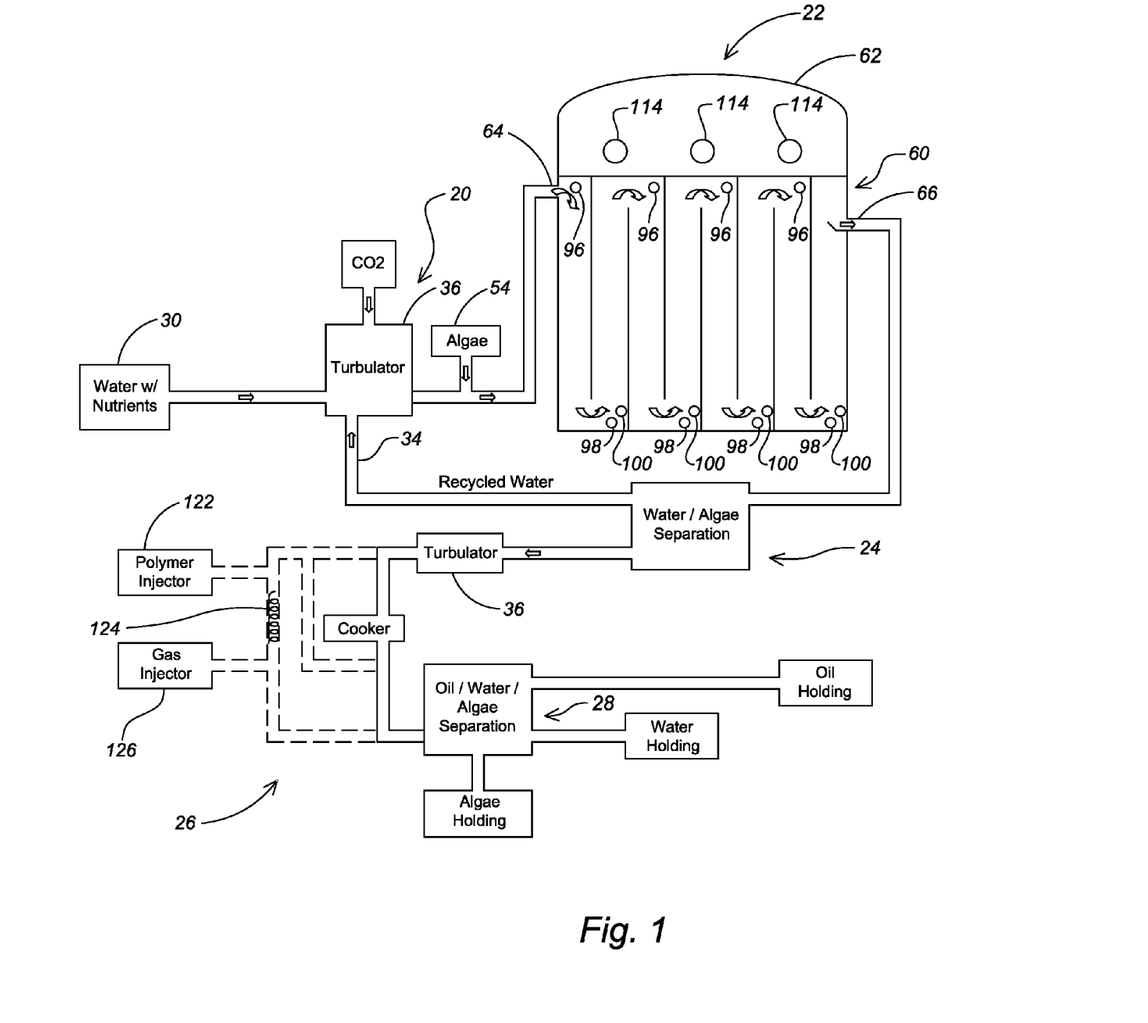
FIG. 1 is a schematic flow diagram of an embodiment of a system for the production and harvesting of algae, included in the system is a photobioreactor with high and low baffles forming a serpentine path of the growth media.

Referring to the drawings more particularly by reference character, FIG. 1 is a schematic flow diagram of a system for the production and harvesting of algae. In major part, the system includes:

(1) a first section 20 for forming an algae growth media;

(2) a photobioreactor 22 in which algae form an algae slurry;

(3) a separation section 24 in which water is extracted from the algae slurry to provide spent media which is reconditioned into reconditioned water for recycle and an algae sludge;

(4) a pretreatment section 26 in which the cells in the algae sludge are broken up; and, (5) a section 28 in which pretreated algae sludge is separated into oil, water and algae fractions.

Figure 2:
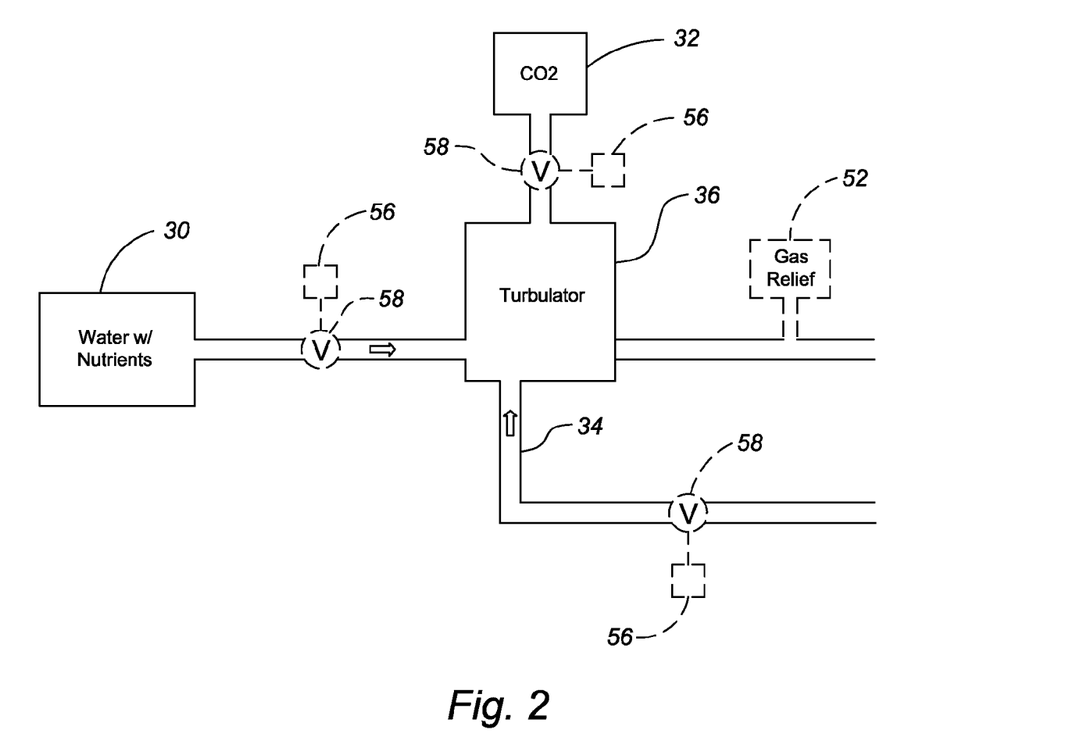
FIG. 2 is a flow diagram for the preparation of a growth media for algae.
Figure 3:
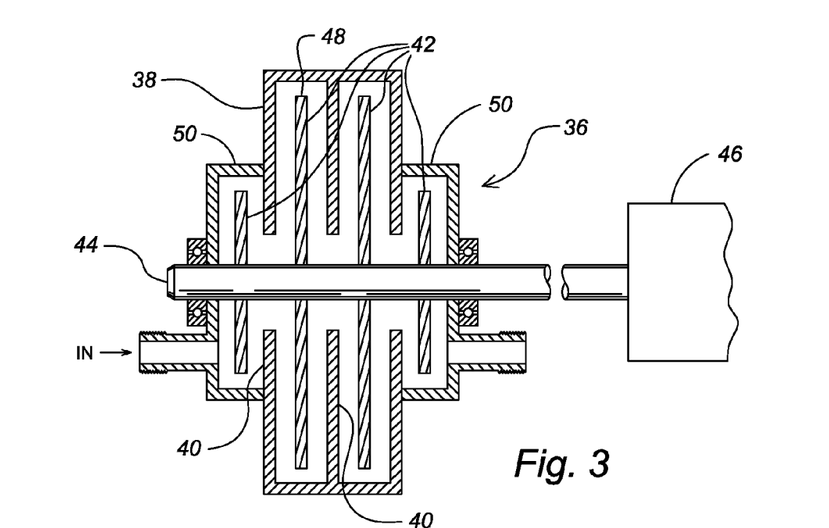
FIG. 3 is a schematic cross-section of a turbulator.

In first section 20, as shown in FIG. 2, a source of water 30, carbon dioxide 32 and reconditioned water 34 are mixed in a turbulator 36. Turning then to FIG. 3, turbulator 36 includes a mixing chamber 38 with interleaved stationary discs 40 and rotating discs 42. Rotating discs 42 are mounted on a shaft 44 which is driven by a motor 46. The rotating discs 42 spinning between the stationary discs 40 create a great amount of turbulence due to boundary layer adhesion. This turbulence puts the carbon dioxide into solution thus creating a favorable growth media for algae. The mixing ratio of gas to water may be controlled by a computer which takes into account the temperature of the water or reconditioned water, the temperature of the media in photobioreactor 22, the density of algae slurry formed in the photobioreactor and the stage of growth the algae are in. When all of these factors are balanced for optimum performance of the algae very little of the carbon dioxide will escape from the water surface of the photobioreactor. If some does escape, it will be captured for recycle as described below.

With continuing reference to FIGS. 2 and 3, a section 48 of a 14" ID pipe is sandwiched between 8" ID pipe sections 50 with stationary discs 40 and rotating discs 42 arranged as shown. Nutrients may be added to the make up water 30 or to the reconditioned water 34. A gas relief 52 may be provided to bleed off carbon dioxide that does not go into solution in the media as it exits turbulator 36. This gas may be recycled back to carbon dioxide source 32.

The carbon dioxide 32 can be a waste gas from an industrial process, combustion exhaust gas, power plant flue gas, or any other selected waste gas source containing carbon dioxide such as the effluent from a lime plant. The gas may be a mix of plant exhaust gases from which particular matter has been removed and may include other greenhouse gases such as carbon monoxide, methane, hydrofluorocarbons, perfluorocarbons as well as various sulfur ($SO_x$) and nitrogen containing compounds ($NO_x$). Some pretreatment of the gases in carbon dioxide source 32 may be required depending on the choice of the algae being grown in photobioreactor 22.

A source of algae 54 is added to the media formed in first section 20. The algae 54 may be naturally occurring, derived therefrom, manipulated or created by artificial means or otherwise cultivated. Algae 54 may be a genetically selected strain most suitable for the production of petro-like products, absorption of carbon dioxide or other purposes. Alternatively (or additionally), the algae may be an existing oil-producing algae known for producing oil based by-products and, as discussed below, algae 54 are preferably selected to use the wavelength, intensity and duration of the artificial light provided in photobioreactor 22 as described below. When the process is operated continuously, it may not be necessary to inoculate the media with algae as it enters photobioreactor 22 as there may be sufficient algae left behind in the photobioreactor to serve as an inoculum. A shown in FIG. 2, the addition of the make-up water and nutrients 30, carbon dioxide 32 and reconditioned water 34 may be under computer controlled 56 valves 58.

Having completed a discussion of first section 20 wherein the algae growth media is prepared, attention is now turned to photobioreactor 22. Photobioreactor 22 includes a cultivation vessel 60 with a cover 62 which encloses vessel 60. An inlet 64 is provided for receipt of the algae growth media formed in section 20 and an outlet 66 is provided for discharge of the algae slurry grown in the photobioreactor to separation section 24. Cover 62 serves several purposes including preventing evaporation, regulating gas transfer, retaining heat and preventing contaminant materials from entering cultivation vessel 60.

Figure 5:
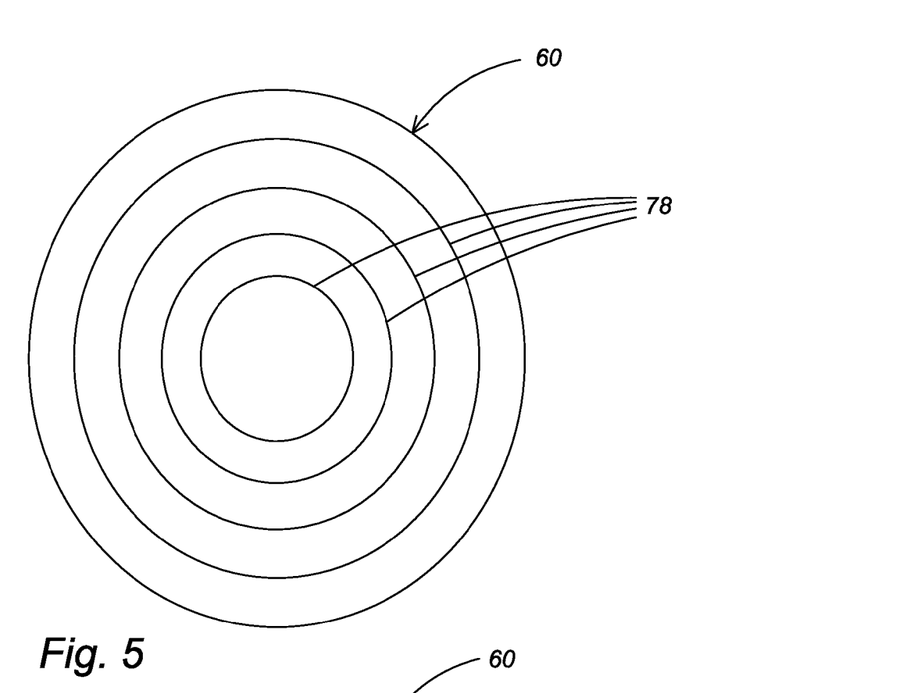
FIG. 5 is a simplified plan view of a second photobioreactor.

Cultivation vessel 60 has a bottom wall 68 and sidewalls 70 and can have many different shapes. In some embodiments, sidewalls 70 are perpendicular to bottom wall 68 and are joined with perpendicular end walls 72 so that cultivation vessel 60 is rectangular in shape. Cultivation vessel 60 may take of a variety of other shapes such as circular as shown in FIG. 5, square, triangular, hexagonal as well as other symmetrical and asymmetrical shapes. In other embodiments of the subject system for the production and harvesting of algae a plurality of individual cultivation vessels 60 may be interconnected in series with common sidewalls 70 and/or end walls 72 to reduce building costs.

Figure 17:
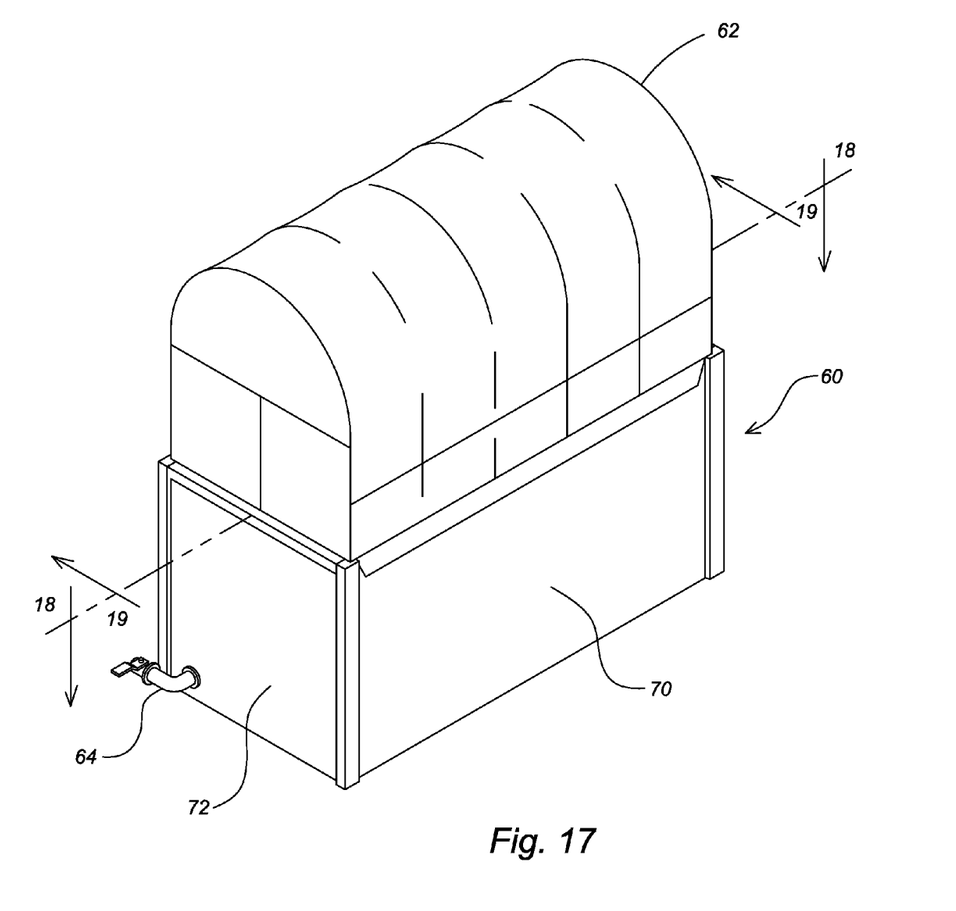
FIG. 17 is a perspective view of a photobioreactor constructed from a freight container.
Figure 18:
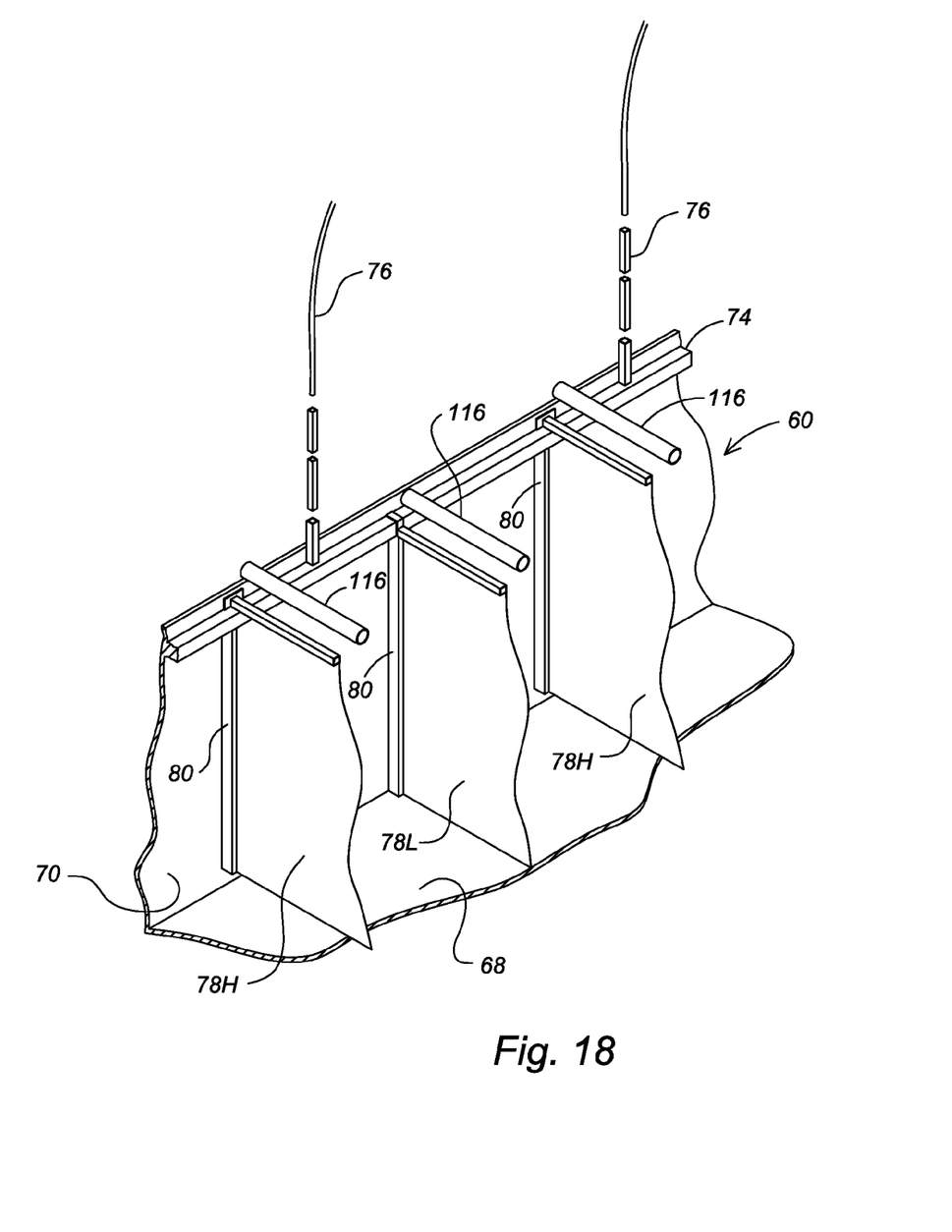
FIG. 18 is a perspective detail showing the interior of the freight container shown in FIG. 17.

In the form illustrated in FIGS. 17-18, cultivation vessel 60 is a freight container with bottom wall 68, sidewalls 70, end walls 72 and with a sideboard 74 that encircles the top of the vessel. Cover 62 is supported on spaced apart hoops 76 which are attached to sideboard 74. The freight container (i.e., cultivation vessel 60) illustrated in FIGS. 17-18 is constructed of corrugated weathering steel and is 8 feet (2.44 m) wide by 8 feet (2.44 m) high and is a nominal 20 feet (6.1 m) long. Container 60 has a door fitted at one end and is reinforced with tie rods extending between the sidewalls 70 with one or more horizontal brace bars attached to the outside of the door.

Figure 6:
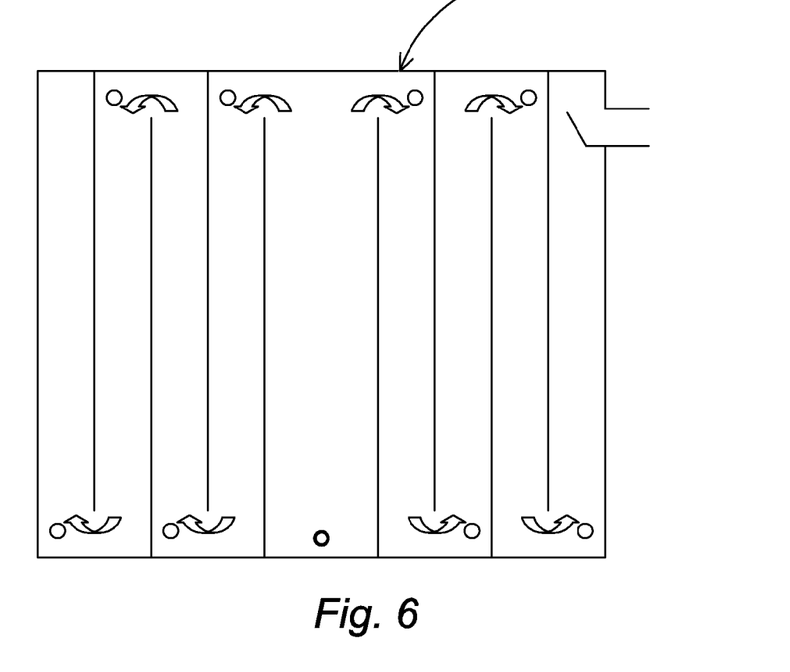
FIG. 6 is a simplified cross-section of the second photobioreactor.

A plurality of baffles 78 are provided in cultivation vessel 60 between an upstream end wall 72 and a downstream end wall 72. Baffles 78 may be rigid or flexible if support by an appropriate frame. By using a series of baffles 78 that force the flow of the media up and over alternate baffles 78, a channel is formed which increases the residence time of the algae slurry in photobioreactor 22. As illustrated in FIG. 18, baffles 78 are parallel to each other but in other embodiments may be angled with respect to each other or concentric as shown in FIGS. 5-6 or the like. Baffles 78 are arranged in an alternating high and low baffles 78H, 78L to form generally vertical bioreactor cells with return end channels. Low baffles 781L are sealed water-tight to bottom wall 68. As shown in FIG. 1, for example, the first vertical bioreactor cell starts at the top of vessel 60 at upstream end wall 72 and passes downwardly to the open lower end of the first high baffle 78H, the second vertical bioreactor cell starts at the bottom of first high baffle 78H and passes upwardly to the top of low baffle 78L. This arrangement is repeated in cultivation vessel 60 to provide a serpentine flow channel through the bioreactor cells between high baffles 78H and low baffles 78L which increases the residence time of a culture of algae flowing through photobioreactor 22. Baffles 78 may be supported on air or water inflated flexible seals such that the spacing between baffles 78 is adjustable. This feature allows for the spacing between baffles 78 to be easily adjusted to create smaller or larger bioreactor cells. In other embodiments as shown in FIG. 18 baffles 78 may be sandwiched between vertical wood ribs 80 which are attached to sidewalls 70 of vessel 60 with the proper spacing.

In the photobioreactor 22 shown in FIGS. 17-18, there are ten baffles 78 which are spaced 23" apart. Baffles 78 are constructed using a plastic pipe or suitable material for a frame on which a webbing of heavy duty plastic fabric is supported. For this purpose, the side edges of fabric may be folded over to form a channel through which the members of frame may be threaded. At the top of vessel 60, low baffles 78L may be about 2" lower than the adjacent high baffle 78H. A similar 2" spacing may be provided between high baffle 78H and bottom wall 68. This arrangement permits the growth media and developing algae slurry to flow over the top of low baffles 78L and under the adjacent high baffles 78H.

Figure 19:
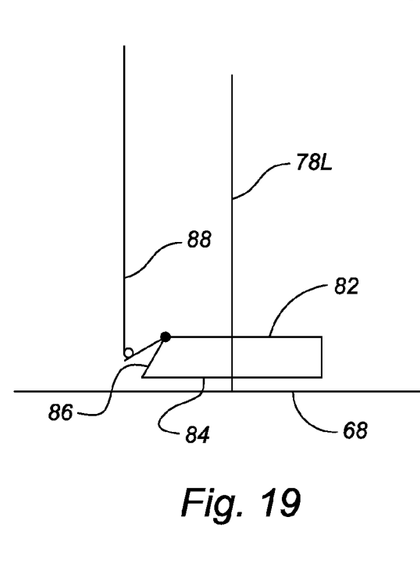
FIG. 19 is a detail showing an antibackflow valve on one of the low baffles

An antibackflow valve 82 as shown in FIG. 19 may be provided at the bottom of each low baffle 78L. Antibackflow valve 82 is normally closed but opens when there is a predetermined pressure deferential between the bioreactor cells. The purpose of antibackflow valve 82 is to equalize the water level in the bioreactor cells during filling or emptying of photobioreactor 22. As shown in FIG. 19, antibackflow valve 82 is a section of pipe 84 with a flap lid 86 hinged at one end. A rope 88 is attached to flap lid 86 to facilitate control of the flow between the bioreactor cells during filling or emptying of vessel 60.

Figure 14:
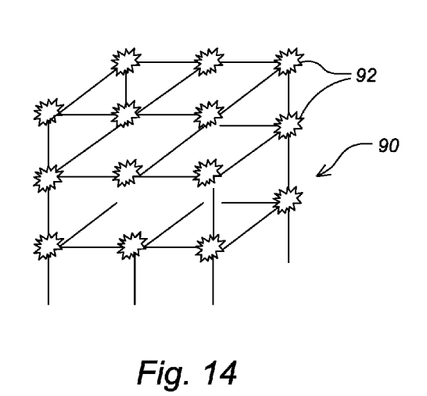
FIGS. 14-16 are simplified views of various arrangements of LEDs in a photobioreactor.
Figure 15:
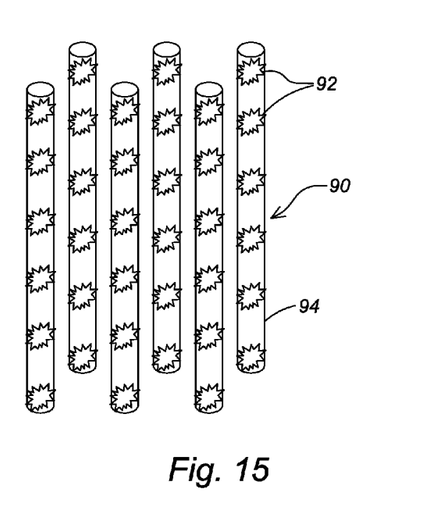
Figure 16:
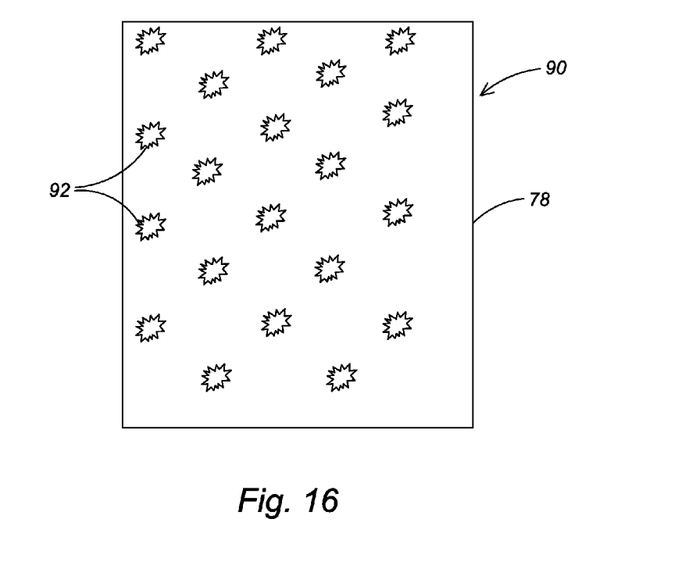
Figures 20, 21:
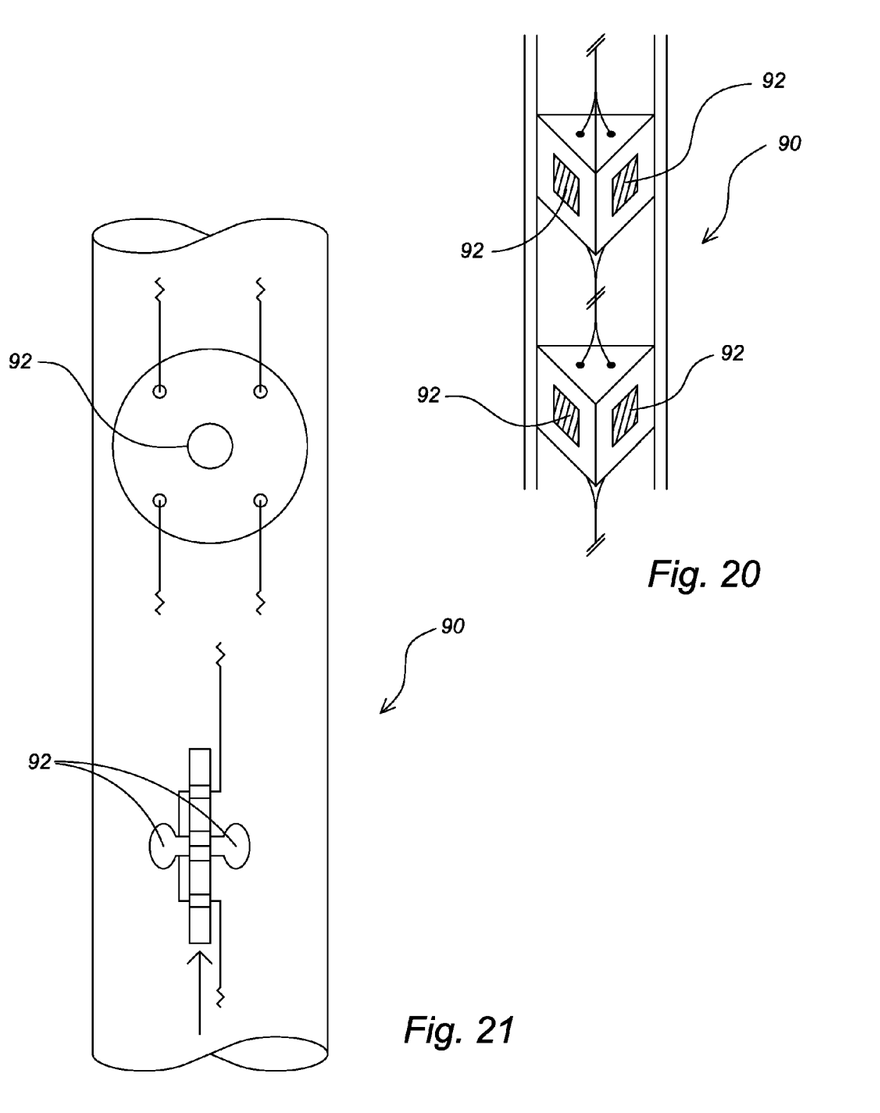
FIG. 20-21 are additional views of various arrangements of LEDs in the photobioreactor.

Cover 62 may be formed of a clear plastic material. Additional light is provided by a light source 90 capable of stimulating photosynthesis in the algae. Light source 90 may be a light curtain or as shown in FIGS. 14-16, an array of LEDs 92 arranged in a two- or three-dimensional grid suspended in the photobioreactor cells or attached to baffles 78. In some embodiments, light source 90 may be removable from the photbioreactor cells, for example for cleaning. In the form illustrated in FIG. 15, the LEDs are strung in a plastic tube 94 which may be attached to baffles 78. Air may be circulated through tube 94 for controlling the temperature of the media in photobioreactor 22. Other examples of LED arrays for use in the space between the baffles are shown in FIGS. 20-21. As shown in FIG. 20, each LED 92 has a 120 degree spread of light. To achieve a 360 spread of light, the LEDS may be strung in a three-light cluster. As shown in FIG. 21, each LED 92 has a 180 degree spread of light. In this case, a 360 spread of light can be achieved when the LEDs are strung back to back on a plastic washer. The above mentioned light sources do not limit the scope of light sources 90 suitable for photobioreactor 22 but serve the purpose of illustrating some of the present technology Improvements in lighting technology and efficiency will be readily adaptable to the present photobioreactor 22. It is also contemplated that natural sunlight may be used. For example as mentioned above, cover 62 may be formed of clear plastic and sunlight may be captured with large Fresnel lenses and focused on an input end of a bundle of fiber optic cables. These small light pipes may be used to conduct the light into the photobioreactor cells and distribute it evenly.

The wavelength, intensity and duration of the light applied by light source 90 should be selected to complement the requirements of the algae. For example, it is known that blue-green and green algae strains optimally function by photosynthesis to sequester carbon dioxide when exposed to light having wavelength in the range of, generally 400-700 nanometers. Excessive intensity should be avoided as it may lead to photo inhibition and photo oxidation, while too low intensity may not promote algal growth. Duration of light exposure is also important as some algae such as blue-green algae require a light-dark cycle. On the other hand, as another example, the natural, day-night diurnal cycle of blue-green algae may be compressed by light source 90 by using flashing LEDs, preferably by flashing them with an on-period ranging from 1 nanosecond to 10 seconds and an off-period ranging from 1 nanosecond to 10 seconds.

Figure 4:
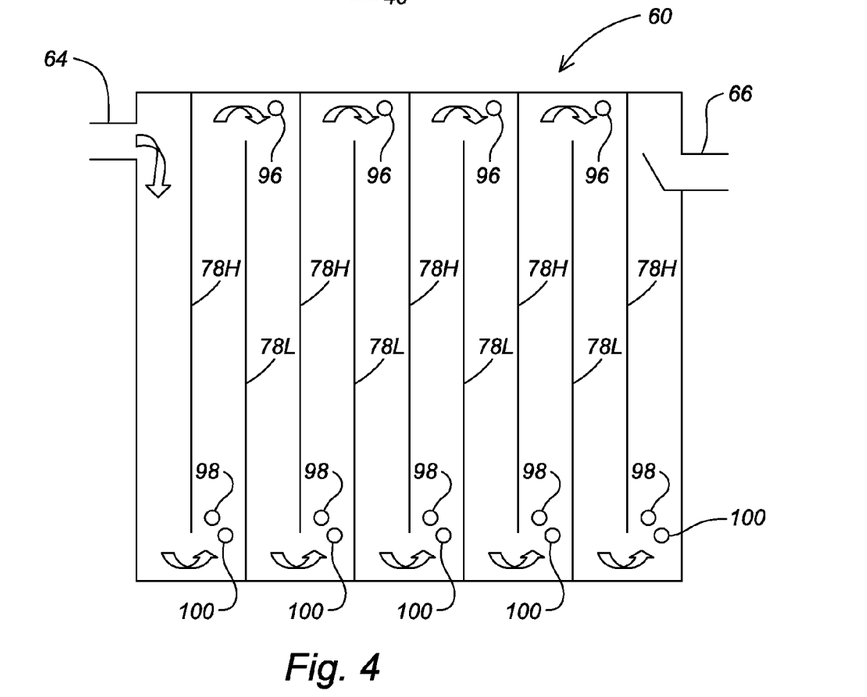
FIG. 4 is simplified cross-section of a first photobioreactor.

Flow through photobioreactor 22 may be promoted by flowing cold media or reconditioned water through outlets 96 (FIGS. 1 and 4) at the top of vessel 60 or warm media or reconditioned water through outlets 98 at the bottom of vessel 60. Pumping cold liquid at the top of the photobioreactor cells causes the lighter less dense water to move down and pumping warm water at the bottom of the photobioreactor cells causes the warmer less dense water to move up. Alternatively (or additionally) carbon dioxide may be injected through outlets 100 at the bottom of vessel 60 causing upward flow. The gas outlets 100 may comprises any type of suitable gas jet. In a preferred embodiment, outlets 100 comprises a gas diffuser which breaks up the introduced gas into smaller, more soluble bubbles. As the fluid passes the gas injectors that particular portion of the media becomes less dense than the surroundings and has an inclination to rise which creates upward flow. As the algae consume the carbon dioxide, the culture media becomes denser causing the media to move down the other side of the baffle. More carbon dioxide may be pumped into vessel 60 in front of the next low baffle 781L which again makes the algae/water mix less dense which again leads to rising. As this process repeats, the algae slurry gets denser until it reaches the point that more water may be added through water outlets 96 and/or 98. A pump is another alternative for causing the media to circulate up and over baffles 78 and through vessel 60 between inlet 64 and outlet 66.

Figure 8:
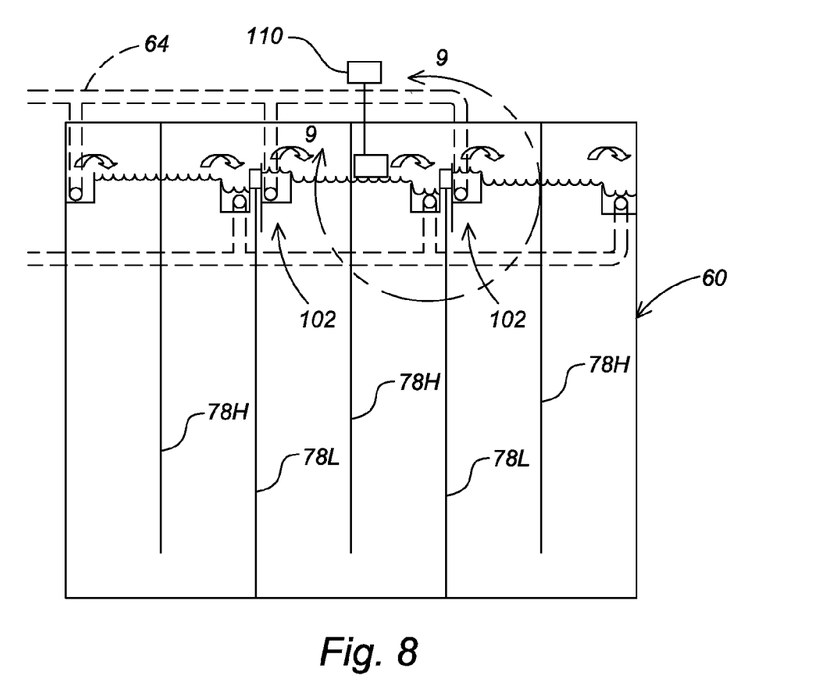
FIG. 8 is a schematic cross-section of a dual-purpose gutter system for use in a photobioreactor.
Figure 9:
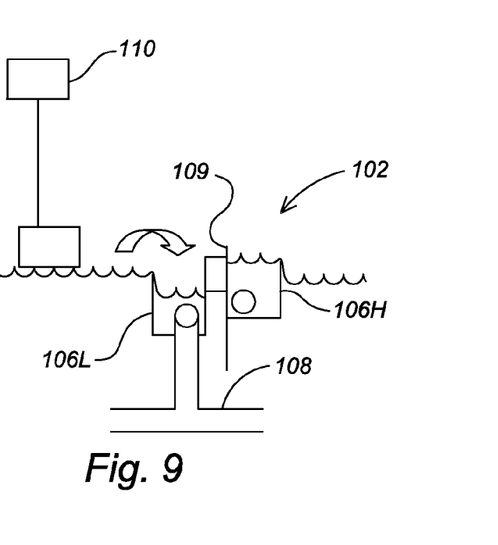
FIG. 9 is a cross-section on an enlarged scale.

Turning now to FIGS. 8-9, a clamp-on gutter system 102 is illustrated. Media is flowed evenly into high gutter 104H and into the photobioreactor cells. The algae slurry is collected in low gutter 106L as it passes over low baffles 78L. The slurry collected in low gutters 106L is gravity flowed through one of sidewalls 70 into a manifold 108 for pretreatment and harvesting as described below. A dam 109 (see FIG. 9) is provided to prevent backflow between high gutter 104H and low gutter 106L on each clamp-on gutter system 102. A float 110 may be provided to monitor the water level in the photobioreactor cells. The float 110 may be under computer control 112 and connected electronically to variable flow pumps that supply replacement media and/or reconditioned water to the photobioreactor cells. If float 110 is adjusted higher then more water will enter photobioreactor 22 causing the water level to rise which will increase the flow rate towards the discharge points (i.e., low gutters 106L and vessel outlet 66). If the flow rate is increased, there will be less time for the algae to grow and the algae slurry will be less dense which will increase the light efficiency. The computer program may be used to control the height of the float according to the density of the algae slurry at the harvest point (low gutters 106L). In the 20' long photobioreactor shown in FIGS. 17-18, containing 9,500 gallons of media, there are five low gutters 106L. This could permit vessel 60 to be used to grow five different species of algae at the same time with each photobioreactor cell between low gutters 106L holding 1,900 gallons of algae/water mix.

Figure 7:
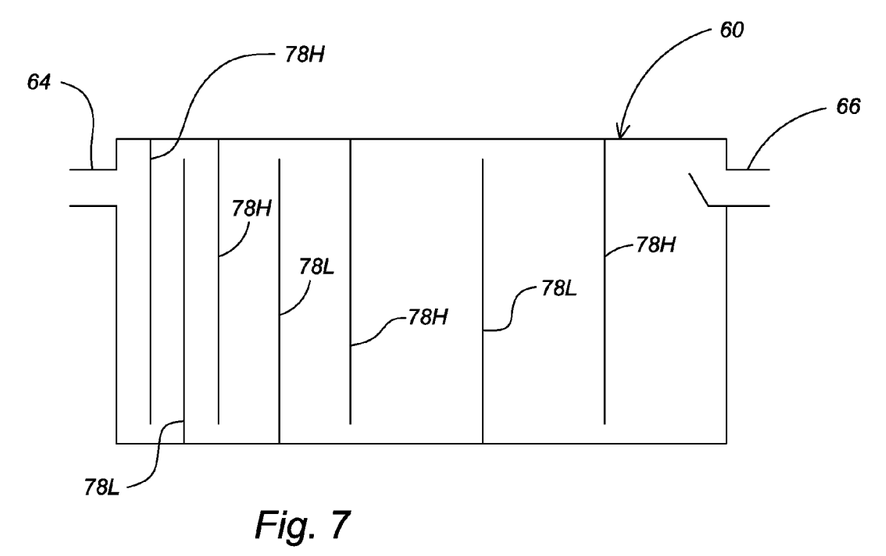
FIG. 7 is a simplified cross-section of a third photobioreactor.

The density of the algae per unit volume in photobioreactor 22 is very important to growth and making sure that there is enough artificial light, nutrients and carbon dioxide is a constant challenge because light penetration in the slurry decreases by about 50 percent for every doubling of algae numbers. To address this problem, additional media or reconditioned water may be pumped into the photobioreactor cells such that cell density is reduced. Another option is to harvest the algae as the algae slurry passes over each low baffle 78L in low gutters 106L as described above. This will lead to a lower cell count of algae and therefore better growing conditions for the remaining algae. Another strategy is to increase the photobioreactor cell size in vessel 60 as shown in FIG. 5 and FIG. 7 which will have the effect of diluting the algae slurry and reducing its density. Alternatively (or additionally) more artificial light (LEDs) may be provided as the algae slurry becomes more dense.

Because all strains of algae, both natural and genetically modified, have their own growing requirements. Photobioreactor 22 may be equipped with a system to monitor important conditions including but not limited to: temperature, algae density and cell count, light intensity, pH levels, turbulence, carbon dioxide and oxygen levels and nutrient levels. Using data gathered by the monitoring system the environment in vessel 60 may be changed by adjusting the temperature, watering down the medium to lower algae density and correcting other conditions to a more optimal level. Monitoring and optimizing these variables will provide near perfect growing conditions for the algae.

One of the advantages of the present photobioreactor 22 is that it has a closed top under which oxygen, a by-product of photosynthesis, may be collected and vented through pipes 114 and unconsumed carbon dioxide may be collected and vented for recycling as shown in FIG. 1. For this purpose, collection pipes 114 for the oxygen may be a slotted plastic well pipe with a sleeve membrane that is permeable to oxygen only. Oxygen collection pipes 114 may be connected to a gas compressor and routed to a storage tank.

In addition to facilitating the collection of oxygen and remaining carbon dioxide, cover 62 also reduces the risk of unwanted contaminants including bacteria and foreign strains of algae. As a precaution as shown in FIG. 19, UV lights 116 may be used to kill any bacteria or foreign algae that do occur. This may be accomplished by treating the algae slurry as it comes over the top of the first low baffle 78L and successive baffles. A hood may be provided over the top of the UV lights that run the entire length of the baffle. Positive pressure under cover 62 may be created and maintained by an air delivery system that filters all particulates from the air stream and is treated with UV light and other appropriate technologies to remove or kill microorganisms in the incoming air. As shown in FIG. 17, cover 62 may be at least as tall as vessel 60 is deep.

The algae slurry exiting low gutters 106L through manifold 108 and/or through outlet 66 of vessel 60 are fed to separation section 24 where water is extracted from the algae slurry. This can be accomplished by gravity, centrifugation or decanting with the reclaimed water being spent media which can be reconditioned for recycle. The recycled liquid may be UV sterilized to kill any contaminant organisms and additional nutrients and water may be added to make up for the loss water in the separation section. The algae sludge may then be used to produce a variety of useful products such as shown in harvesting section 28.

Figure 10:
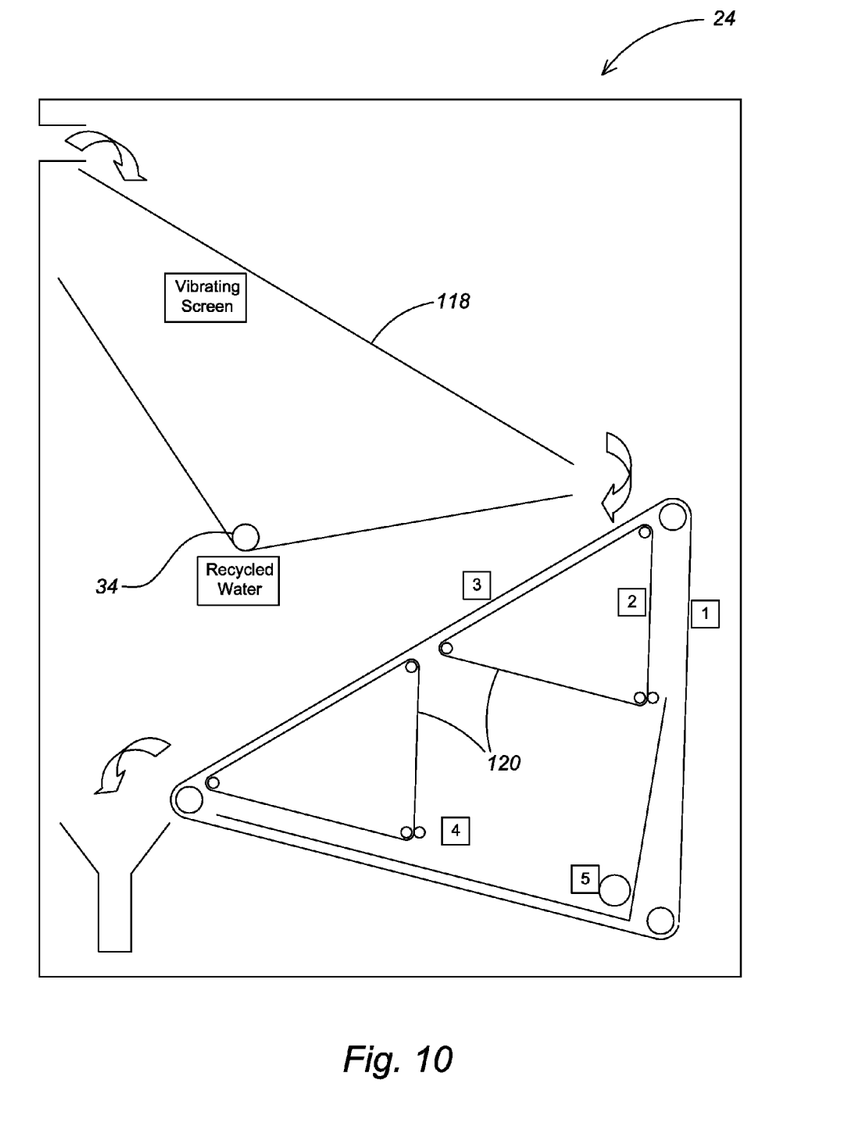
FIG. 10 is a schematic cross-section of a water/algae separation system for an algae slurry.

As shown in FIG. 10, the algae sludge exiting low gutters 106L and/or outlet 66, may be passed over a vibrating screen 118 and then to a pair of absorbent belt dewatering devices 120. The water separated by vibrating screen 118 comprises spent media and may be reconditioned for recycle. The dewatered algae sludge coming off vibrating screen 118 may be further dried on absorbent belt dewatering devices 120. The oil from the dried algae may then be extracted and refined into biodiesel, jet fuel or some other oil based product as described below. The biomass that is left over from the oil removal is also a marketable product for use as a protein supplement, alternative fuel, pharmaceutical, etc.

The algae sludge coming from separation section 24 may be subjected to pretreatment section 26 before oil is extracted. As shown in FIG. 1, the dewatered algae sludge may passed through a turbulator 36 similar to the turbulator used to solubilize the carbon dioxide in the algae growth media. Turbulator 36 tears the algae cells apart and liberates the oil that was encapsulated therein. For further processing, the dewatered algae sludge may be treated with a polymer 122, passed through a static mixer 124 and injected with gas 126 such that micro gas bubbles attached to the oil micro droplets.

Figure 11:
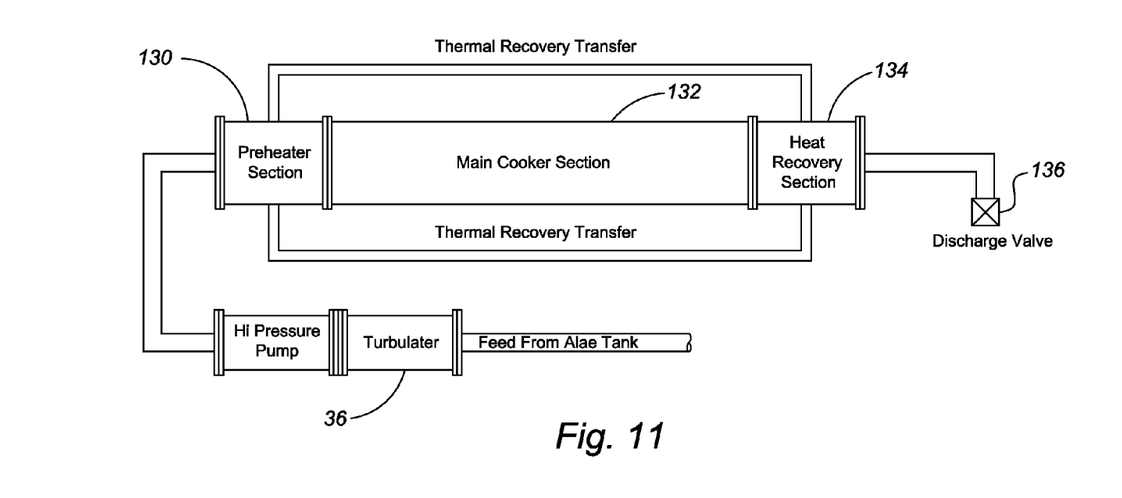
FIG. 11 is a flow diagram showing pretreatment an algae sludge in a cooker.
Figure 12:
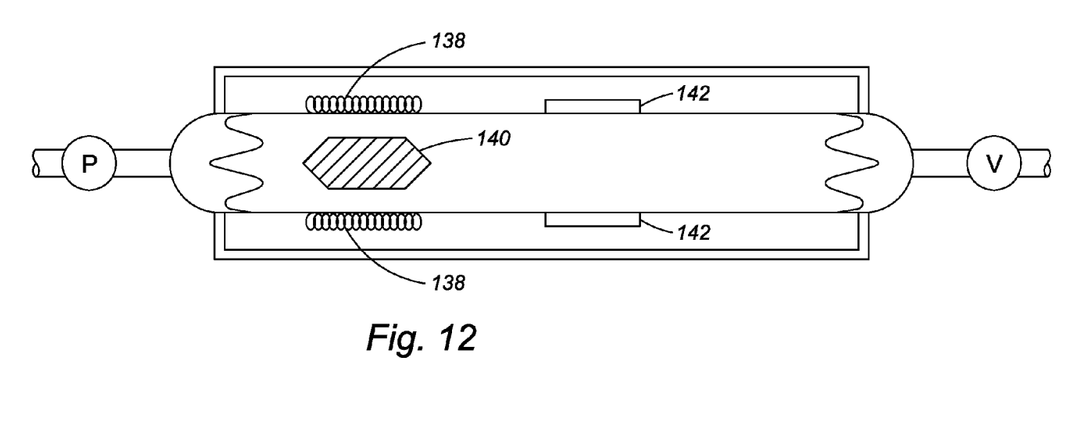
FIG. 12 is a schematic cross section of the cooker.

Alternatively as shown in FIG. 11, the dewatered algae sludge from turbulator 36 may be pumped with a high pressure pump 128 (e.g., between 30 and 90 psi) into a preheater stage 130 of a cooker 132, where reclaimed heat is used to pre-heat the algae slurry before it enters the cooker. Cooker 132 may operate at about 300 degrees F. and 30 psi. After spending 30 minutes or so in cooker 132, the hot, cooked algae is passed through a heat recovery section 134 where heat is reclaimed and transferred back to preheater section 130. A discharge valve 136 meters the cooked algae in a controlled manner for treatment with polymer 122 and gas 126 as described above, whereupon the material is passed to section 28 for separation of the pretreated algae sludge into oil, water and biomass fractions. Details of cooker 132 are shown in FIG. 12 wherein it is illustrated that an induction coil 138 is used to heat a magnetically inducible "pig" 140. Additionally (or alternatively), other heating means 142 such as electric blanket heaters or internal rod heaters may be used to cook the algae. As set forth above, polymer 122 may be added to the cooked algae, passed through static mixer 124 and injected with gas 126.

Figure 13:
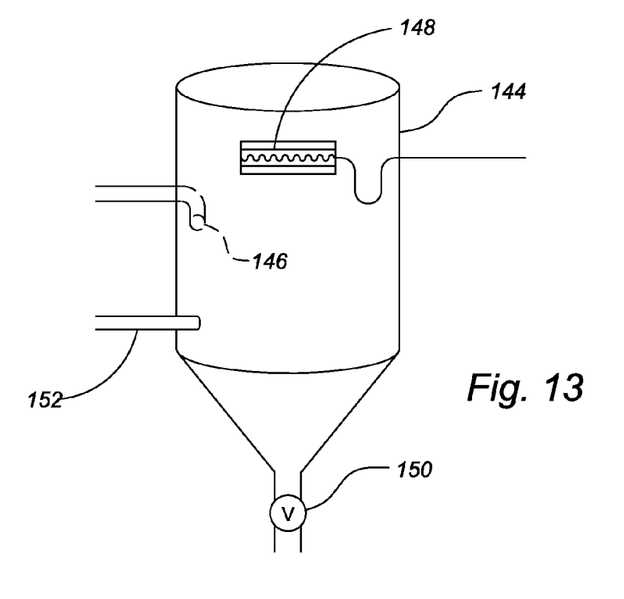
FIG. 13 is a simplified perspective view of an oil/water/algae separation system.

A simplified perspective view of a large settling tank 144 is shown in FIG. 13 wherein the cooked algae from cooker 132 is released under pressure through a pipe 146 parallel to the tank wall. A floating oil collector 148 connected to an oil exit pipe is provided in tank 144. As the processed algae parts and oil come into the settling tank 144 under pressure, the pressure is released and the micro bubbles of gas rise towards the surface of the liquid and attach to the oil micro droplets on the way up. Biomass is discharged through valve 150 and spent media for reconditioning through water exit pipe 152.

As various changes could be made in the above constructions without departing from the scope of the invention, it is intended that all matter contained in the above description or shown in the accompanying drawings shall be interpreted as illustrative and not limiting.

What is claimed is:

1. A photobioreactor comprising a vessel inoculated with algae capable of sequestering carbon dioxide by photosynthesis, said vessel having a bottom, sidewalls, a cover, an inlet for fresh media and an outlet for a harvestable algae slurry formed in the vessel, a plurality of vertical baffles sealed to the sidewalls and arranged such that alternating high and low baffles are sealed to the bottom and spaced from the bottom, a light source associated with each baffle, said light sources suspended between or attached to the baffles and being capable of stimulating photosynthesis in the algae, and a source of a gas containing at least some carbon dioxide, whereby said baffles provide a serpentine flow path between the inlet and outlet increasing the residence time of the algae in the presence of the light sources, said photobioreactor further having a clamp-on gutter system attached to each low baffle with a low gutter on the inlet side and a high gutter on the outlet side of the vessel, said low gutter attached by a conduit to a manifold for harvesting some of algae slurry formed in the vessel and said high gutter attached to a conduit for supplying make up water or media.

2. The photobioreactor of claim 1 wherein the baffles are light curtains, said light curtains serving as the light source.

3. The photobioreactor of claim 1 wherein the light source is a plurality of LEDs.

4. The photobioreactor of claim 3 wherein the LEDs are strung in tubing through which cooling or heating fluids are flowed for controlling the temperature of the media in the vessel.

5. The photobioreactor of claim 3 wherein the LEDs emit light having a wavelength between 400 nm and 700 nm.

6. The photobioreactor of claim 5 wherein the LEDs are strobed with an on period between about 1 nanosecond and 10 seconds and an off period between about 1 nanosecond and 10 seconds.

7. The photobioreactor of claim 1 further including a computer with a computer control for modulating temperature, pH, carbon dioxide levels, oxygen levels, nutrient levels, flow rate, algae density and light intensity process variables.

8. The photobioreactor of claim 7 wherein the computer control further includes regulators to change one or more of the process variables to optimize the growth of the algae.

9. The photobioreactor of claim 1 wherein the spacing between the baffles increases between the inlet and the outlet.

10. The photobioreactor of claim 1 wherein carbon dioxide outlets are provided near the bottom wall on the outlet side of the baffles spaced from the bottom wall.

11. The photobioreactor of claim 1 wherein water outlets are provided on the inlet side and near the top of the baffles spaced from the bottom wall for water or media colder than the media in the vessel.

12. The photobioreactor of claim 1 wherein water outlets are provided near the bottom wall on the outlet side of the baffles spaced from the bottom wall for water or media warmer than the media in the vessel.

13. The photobioreactor of claim 1 wherein the gas is a raw stack gas containing at least some carbon dioxide from which particulate matter has been substantially removed.

14. The photobioreactor of claim 1 wherein the vessel is a freight container with a sideboard that encircles the top of the vessel, said cover supported on spaced apart hoops attached to the sideboard.

15. The photobioreactor of claim 14 with five low baffles which are sealed to the bottom wall and five high baffles which are spaced two inches from the bottom wall, said baffles spaced about 23 inches apart.

16. The photobioreactor of claim 14 wherein an antibackflow valve is provided at the bottom of each low baffle.

* * * * *